(12) United States Patent
Batarseh

(10) Patent No.: US 6,630,172 B2
(45) Date of Patent: Oct. 7, 2003

(54) MICROBICIDAL COMPOSITION CONTAINING POTASSIUM SODIUM TARTRATE

(76) Inventor: Kareem I. Batarseh, 8610 Larkview La., Fairfax Station, VA (US) 22039

(*) Notice: Subject to any disclaimer, the term of this patent is extended or adjusted under 35 U.S.C. 154(b) by 0 days.

(21) Appl. No.: 09/767,035

(22) Filed: Jan. 22, 2001

(65) Prior Publication Data

US 2002/0136780 A1 Sep. 26, 2002

(51) Int. Cl.$^7$ ............... A01N 55/02; A01N 55/04; A01N 55/06; A01N 59/00; A01N 59/06; A01N 59/16; A01N 59/18; A01N 59/20; A01N 59/22

(52) U.S. Cl. ............... 424/618; 424/600; 424/616; 424/617; 424/620; 424/629; 424/630; 424/638; 424/639; 424/641; 424/644; 424/646; 424/649; 424/650; 424/651; 424/652; 424/653; 424/654; 424/655; 424/682; 424/702; 424/722; 424/DIG. 6; 514/184; 514/189; 514/190; 514/191; 514/492; 514/493; 514/494; 514/495; 514/496; 514/497; 514/498; 514/499; 514/500; 514/501; 514/502; 514/503; 514/504; 514/505; 514/635; 514/724

(58) Field of Search ............... 514/492–505, 514/574, 184, 189, 190, 191, 635, 724; 424/617, 618, 620, 629, 630, 638, 639, 641, 644, 646, 649–655, 682, 702, 600, 616, 722, DIG. 6

(56) References Cited

U.S. PATENT DOCUMENTS

| | | | |
|---|---|---|---|
| 3,422,183 A | 1/1969 | Ellison | 424/28 |
| 4,337,269 A | 6/1982 | Berke et al. | 514/494 |
| 4,396,413 A | 8/1983 | Miller et al. | 71/67 |
| 4,425,325 A | 1/1984 | Ritchey et al. | 424/54 |
| 4,758,439 A | 7/1988 | Godfrey | 426/74 |
| 4,830,716 A | 5/1989 | Ashmead | 204/72 |
| 4,847,049 A | 7/1989 | Yamamoto | 422/24 |
| 4,915,955 A | 4/1990 | Gomori | 424/616 |
| 5,102,547 A * | 4/1992 | Waite et al. | 210/501 |
| 5,342,846 A | 8/1994 | Singh et al. | 514/312 |
| 5,389,360 A | 2/1995 | Mobley et al. | 424/49 |
| 5,504,055 A | 4/1996 | Hsu | 504/121 |
| 5,510,315 A | 4/1996 | Kurotsu et al. | 504/115 |
| 5,516,480 A | 5/1996 | Krall et al. | 264/343 |
| 5,516,925 A | 5/1996 | Pedersen et al. | 556/50 |
| 5,616,251 A | 4/1997 | Bataresh | 210/725 |
| 5,708,023 A | 1/1998 | Modak et al. | 514/494 |
| 5,710,252 A | 1/1998 | Weber et al. | 530/356 |
| 5,945,158 A * | 8/1999 | Djokic et al. | 427/216 |
| 6,176,996 B1 * | 1/2001 | Moon | 205/254 |
| 6,242,009 B1 | 6/2001 | Batarseh et al. | 424/618 |

FOREIGN PATENT DOCUMENTS

| | | |
|---|---|---|
| DE | 1 642 001 | 4/1974 |
| EP | 0 041 792 | 5/1981 |
| FR | 2 728 143 | 12/1994 |
| JP | 6-100403 * | 4/1994 |
| JP | 07138167 | 5/1995 |
| JP | 1998 0186163 | 1/1998 |
| JP | 63-222100 * | 9/1998 |
| JP | 10338605 | 12/1998 |
| JP | 11-209209 | 3/1999 |
| WO | WO 94/04167 | 3/1994 |
| WO | WO 95/13700 | 5/1995 |
| WO | WO 96/01231 | 1/1996 |
| WO | WO 97/02038 | 1/1997 |
| WO | WO 97/30057 | 8/1997 |
| WO | WO 97/33477 | 9/1997 |
| WO | WO 99/17735 | 4/1999 |
| WO | WO 00/62618 | 2/2000 |
| WO | WO 00/27390 | 5/2000 |

OTHER PUBLICATIONS

Chemical Abstracts 110: 179576, 1998.*

Chemical Abstracts 106:171123 (1987), abstracting: HU 39320 (Sep. 1986).*

Tzeng et al., "Products in light–mediated reactions of free methionine–riboflavin mixtures that are biocidal to micro-organisms", (Can. J. Microbiol. vol. 36, No. (7), pp. 500–506), STN/CAS, Caplus, Abstract, 1990.

Castillo et al., "Synthesis and spectral properties of new complexes between glycine and titanium (III), vanadium(III), chromium(III), iron(III), cobalt(II), nickel(II) and copper(II)" (Transition Met. Chem. (Weinheim, Ger.)(1984), 9(7),268–70), STN online, file.

M'Hiri et al., "Physicochemical and structural study of metal complexes of L–.beta.–phenylalanine" (J. Soc. Chim. Tunis. (1983), 9, 19–33), STN online, file CAPLUS, Abstract.

(List continued on next page.)

Primary Examiner—John Pak
(74) Attorney, Agent, or Firm—Kilyk & Bowersox P.L.L.C.

(57) ABSTRACT

Disinfectant formulations are described which are preferably ecologically friendly and non-toxic to mammals and plants, and are highly effective against a broad spectrum of detrimental pathogenic microorganisms. The microbicidal formulation contains complexes having at least one metal ion which is microbicidal to at least one microorganism and potassium sodium tartrate in some form. When potassium sodium tartrate is used with these metal ions, it enhances the complex-forming properties of such metal complexes while concurrently increases their efficacy and potency at the same level of metal ion concentrations. These microbicidal formulations can be diluted in suitable proportions into aqueous systems to produce the desired dosages for each individual case, depending on the level and the severity of the contamination. The microbicidal formulations can be applied by conventional methods, e.g., spraying, soaking, fogging, impregnation, and the like. The formulations can also be used as preservatives, such as for fresh or cut flowers and plants. These microbiocides can also be made as gels or solids in different forms by using techniques available to those skilled in the art.

30 Claims, No Drawings

OTHER PUBLICATIONS

Saxena et al., "Electrometric study of divalent zinc, cadmium and mercury complexes of DL–tryptophan" (Trans. SAEST (1981), (1), 45–8), STN online, file CAPLUS, Abstract.

Cusack et al. "Synthesis, Moessbauer and infrared studies of inorganic tin derivatives of amino acids" (Inorg. Chim. Acta (1980), 46 (4), L73–L75), STN online, filed HCAPLUS, Abstract.

Mogilevkina et al., "Antitumor activity of complexes of platinum with acids and peptides" (Onkologiya (Kiev) (1979), 14–40–3), STN online, file HCAPLUS, Abstract.

Volshtein et al., "Complexes of platinum (II) with .beta.–phenyl–.alpha.–alanine" (Zh. Neorg. Khim (1975), 20(12), 3352–6), STN online, file CAPLUS, Abstract.

Kollmann et al., "Preparation and characterization of some amino acid and peptide complexes of gold (I,III), palladium(II), and platinum(II)" (J. Prakt. Chem. (1975), 317(3), 515–19), STN online, file HCAPLUS, Abstract.

Natusch et al., "Direct detection of mercury (II)–thio–ether bonding in complexes of methionine and S–methylcysteine by 1H nuclear magnetic resonance" (J. Chem. Soc. D (1970), (10), 596–7), STN online, file HCAPLUS, Abstract.

Volshtein et al., "Methionine as a tridentate ligand in platinum(II) complexes" (Dokl. Akad. Nauk SSSR (1968), 178(3), 595–7), STN online, file HCAPLUS, Abstract.

Perrin et al., "Histidine complexes with some bivalent cations" (J. Chem. Soc. A (1967), (5), 724–8), STN online, file HCAPLUS, Abstract.

Froment, M., et al., "Influence du Tartrate Double de Sodium et de Potassium sur la Croissance des Depots Electrolytiques D'argent Obtenus a Partir d'une Solution Aqueuse de Nitrate" Comptes Rendus de L'academie des Science, Paris, t271C, pp. 253–256 (1970).

Sumarokova et al., "Interaction of tine dichloride with organic bases" (Teor. Rastvorov (1971) 323–9), STN online, file CAPLUS, Abstract.

Simeon et al., "Chelation of some bivalent metal ions with alanine and phenylalanine", (Croat. Chem. Acta (1966) 38, 161–7), STN online, File HCAPLUS, Abstract.

Khurshid, "Antibacterial activity of iron(II) and zinc(II)–amino acid complexes" (Pak. J. Pharmacol. (1996), 13(1), 41–45), STN online, file HCAPLUS, Abstract.

Ali–Mohamed et al. "Studies on the bacterial activity of cobalt(III), complexes. Part II. Cobalt (III) aminoacidato–complexes" (Transition Met. Chem. (London) (1989), 14 (3), 181–4), STN online, file HCAPLUS, Abstract.

Kawada et al., "Methionine and pentocystine copper salts as bactericides and fungicides" (1974, JP 49012028), STN online, file HCAPLUS, Abstract.

Yoshida et al., "Methionine zinc salt for the control of Alternaria mali" (1976, JP 51112517), STN online, file HCAPLUS, Abstract.

Tumanov et al., "Antimicrobial activity of copper (II) coordination compounds with .alpha.–amino acids" (Izv. Akad. Nauk Mold. SSR, Ser. Biol. Khim. Nauk (1983), (6), 44–6), STN online, file HCAPLUS, Abstract.

Ackermann et al., "Preparation of substituted phenylalanine– metal complexes having fungicidal activity" (1989, DD 267731), STN online, file HCAPLUS, Abstract.

Jain et al., "Some new metal chelates of L–lysine monohydrochloride as potential antifungals" (Indian J. Phys. Nat. Sci. (1983), 3(A), 51–2), STN online, file HCAPLUS, Abstract.

Van Nostrand's Scientific Encyclopedia ($8^{th}$ Ed. 1995), pp. 618, 619.

Goodman and Gilman's, The Pharmacological Basis of Therapeutics ($7^{th}$ Ed. 1985), pp. 962, 963, 968.

Ohtaki et al., "A potentiometric study on complex formation of silver(I) ion with glycine and beta–alanine in aqueous solution", Bull. Chem. Soc. Jpn., vol. 53 (1980), pp. 2865–2867.

Gowda et al., "Interaction of acidic amino acids with bivalent metal ions," J. Electrochem. Soc. India., vol. 30, No. 4 (1981), pp. 336–340.

Brady, et al. General Chemistry Principles and Structure (Third Edition), Chapter 4, pp. 126 and 127, 1982.

Menabue, et al., "Silver(I) Complexes with N–Protected Amino Acids", Inorganic Chimica Acta, 46, (1980) L77–L78.

John R.J. Sorenson, "Copper Chelates as Possible Active Forms of the Antiarthritic Agents", Journal of Medical Chemistry, 1976, vol. 19, No. 1, pp 135–148.

WPIDS Abstract, accession No. 1994–156517 (1994).*

* cited by examiner

MICROBICIDAL COMPOSITION CONTAINING POTASSIUM SODIUM TARTRATE

FIELD OF THE INVENTION

The present invention relates in general to controlling microorganisms and more particularly relates to microbicides which are preferably environmentally friendly and non-toxic to mammals and which are highly effective against viruses, amoebea, bacteria (both gram-negative and -positive), fungi, algae, spores, yeast, and the like.

BACKGROUND OF THE INVENTION

Water is the most important element of life since it comprises almost 80% of the human body. In addition, food hygiene depends solely on water, and therefore contamination of water is a common vehicle for the transport of epidemic diseases to humans like Typhoid, food poisoning, and Dysentery. For example, Psychrophilic bacteria's presence in the micro-flora in water can affect refrigerated food and spoil it. Hence, water contamination cannot be overlooked and extreme measures should be taken to assure a high quality of water to sustain life.

With the advent of technology, clean water is becoming a scarce commodity. Water contamination is unequivocally becoming a worldwide problem with unknown ramifications, and billions of US dollars are spent annually to improve its quality. Contamination of waters is not only restricted to industrialized countries, but includes developing nations as well. Therefore, there is an immediate need to find poignant solutions to maintain and preserve water sources.

Recently, there has been a growing interest among scientists and engineers to develop new water and food disinfectant technologies to clean water from dangerous microorganisms. Various methods have been employed which are divided into two categories; namely, physical, chemical, or both. The physical category is represented by techniques utilizing ultrafiltration, reverse osmosis, radiation, freezing, heating, and ultrasound. Although these methods have proved to be effective, the drawbacks include the large electricity requirements and expensive equipment. On the other hand, the chemical category relies on the use of chemical adjuvants which exhibit biocidal properties such as aldehydes, phenols, alcohol, potassium permanganate, and chlorine and certain chlorine containing compounds. Some of these chemicals have many disadvantages associated with them and are now considered poisonous compounds. For instance, people coming into contact with these substances can develop skin irritation and suffer from long time illnesses which in some cases can be fatal; not to mention the unpleasant taste and odor associated with these chemicals. In addition, formation of mutagenic and carcinogenic agents, and genetic resistance are also some of their disadvantages. Notwithstanding, such compounds have afforded a way to battle these harmful microorganisms and their effectiveness have been unequivocally demonstrated.

Other methods have relied upon the use of ultra-violet irradiated silver fluoride solutions containing silver as a source of germicide activities, such as U.S. Pat. No. 3,422,183, incorporated herein in its entirety by reference. However, such techniques require expensive equipment and large amounts of electricity.

Hydrogen peroxide is a strong oxidizing agent, and it has been used for the past 40 years as a disinfectant. Its main advantage is that it does not produce toxic residue or by-products. It has been used ubiquitously as an indirect food additive, as a disinfectant in hospitals, as a decontamination and purification agent of industrial waste water, and as a cleaning agent for exhaust air. Nonetheless, it decomposes readily to form water and oxygen, and has high sensitivity to sunlight and UV rays. Therefore, it is not suited for long-term use since recontamination cannot be circumvented.

In 1880, the Swiss botanist Carl van Nageli observed that highly diluted silver solutions have an algicidal effect. To describe this effect he coined the term "Oligodynamic". Colloidal silver, which is a pure, all-natural substance consisting of sub-microscopic clusters of silver ions held in suspension in de-ionized water by tiny positive charges on the silver ions, is a powerful prophylactic antibiotic which was used for years with no known side effects. It acts as an inhibitor disabling particular enzymes which bacteria, fungi, and viruses used in their mode of metabolism.

Based on this oligodynamic property, U.S. Pat. No. 4,915,955, incorporated in its entirety herein by reference, combines the germicidal effects of hydrogen peroxide with silver, an inorganic acid, and an organic stabilizer at concentrations of 10–35 mg/l to combat many forms of bacteria and viruses. The process is based on silver ions, with the aid of hydrogen peroxide, damaging the protective biofilms of these microorganisms. Hence, this method depends solely on killing germs intercellularly. Accordingly, there is a need to develop a new generation of microbicidal agents that overcome one or more of the above-described disadvantages.

International Published Patent Application No. WO 00/62618 describes the formation of metal complexes suitable as disinfectants and sanitizers to combat pathogenic microorganisms. It relies on using metal ions and amino acids to form complexes, which serve as carriers for metals, in order to diffuse into the intra-cellular medium of such microorganisms where it exhibits its biocidal activities. The composition can be prepared by mixing a metal salt compound in an aqueous solution, and an inorganic acid at room temperature to adjust the pH of the solution; adding at least on an equimolar basis, depending on the valency of the metals, at least one amino acid to form an insoluble metal complex while homogenizing the mixture; and depending on its use, the resultant solution can then be proportioned with various ratios to make suitable disinfectants either by adding appropriate amount of distilled-deionized water and/or by the addition of chlorhexidine gluconate, chlorhexidine digluconte, chlorhexidine dihydrochloride, chlorhexidine diacetate, isopropanol, and hydrogen peroxide. According to a preferred embodiment, silver nitrate is used as the metal salt; distilled deionized water is used to make up the aqueous medium; phosphoric acid is used as the inorganic acid; glutamic acid is used as the amino acid; and hydrogen peroxide is used as the synergetic disinfectant.

SUMMARY OF THE INVENTION

The present invention relies on using metal ions (M). A chemical matrix or complex is formed from metal ions and potassium sodium tartrate used in at least one fourth (¼) of the stoichiometric amount of the metal ion, depending on the valency of the metal. These concentrated complexes can then be mixed with water to form suitable disinfectants.

A particularly useful application of the disinfectant of the present invention is in the preservation of flowers and plants, as a general disinfectant, sterilization of articles and surfaces and areas, including, but not limited to, food, liquids, (e.g., water, beverages), animal feed, pharmaceuticals, hospitals, surgical equipment, swimming pools, saunas, fish, poultry, cattle, and other farming uses, and the like.

It is to be understood that the preceding general discussion and the discussion which follows are considered explanatory and exemplary in nature, and are solely intended to give additional merits of the current invention, as claimed.

DETAILED DESCRIPTION OF THE PRESENT INVENTION

The present invention provides a suitable concentrate of organo-metal compounds that form suitable disinfectants upon admixing with water or other aqueous sources. The basic principle that governs the formation of such a concentrate is the fact that the metal ions are complexed with potassium sodium tartrate (hereinafter "PST"). The PST or ion thereof is used in at least one-fourth of the stoichiometric amounts or more (based on the metal ion present) to form organic complexes.

To enhance its activity, the concentrated organic complex can be mixed with other disinfectants, including, but not limited to, isopropanol, chlorhexidine gluconate, chlorhexidine digluconate, chlorhexidine dihydrochloride, chlorhexidine diacetate, and/or hydrogen peroxide, though it is not necessary. In addition, natural and artificial color and flavor additives as well as other additives can be added as well.

Of course, the microbicidal formulations of the present invention can be used either directly, by introduction to a system, e.g., a swimming pool, or can be diluted with aqueous solutions, like distilled and/or deionized water to provide the necessary biocidal activity, depending on the application.

With respect to the organic complex, the metal ion(s) complexes with potassium sodium tartrate (hereinafter "PST-M").

Other organic complexes can be used in addition to or in combination with the PST-M complex such as the R-M complexes described in International Published Patent Application No. WO 00/62618, incorporated in its entirety by reference herein. When additional complexes are used, the R group may also include at least one amino acid or can be formed from at least one amino acid. The amino acids are preferably amphoteric, that is, they can react either as acids or as bases, depending on the circumstances. Preferably, examples of amino acids or compounds containing amino acids which can be used as the R group or to form the R group include, but are not limited to, α-amino acids. Specific examples include, but are not limited to, isoleucine, phenylalanine, leucine, lysine, methionine, threonine, tryptophan, valine, alanine, glycine, arginine, histidine, hydroxyproline, α-aminobutyric acid, asparagine, aspartic acid, cysteine, glutamic acid, glutamine, phenylalanine, proline, serine, tyrosine, and derivatives thereof and mixtures thereof.

The complex of the present invention is preferably accomplished by forming the complex under low pH conditions (e.g., acidic conditions) and preferably at pH conditions of pH 2.0 or less and more preferably at a pH 1.5 or less.

With respect to the other part of the complex which is M, M represents at least one monovalent or polyvalent metal ion or cation, which is microbicidal to at least one microorganism. Preferably, the metal ion is microbicidal to a multitude of microorganisms. Examples of the metal ion include, but are not limited to, cations of silver including colloidal silver, copper, zinc, mercury, manganese, chromium, nickel, cadmium, arsenic, cobalt, aluminum, lead, selenium, platinum, gold, titanium, tin, barium, bismuth, vanadium, iron, strontium, antimony, and the like.

Optionally, the PST in the complex of the present invention can replace partially or entirely the amino acid group in the R-M complex described above. The composition thus obtained is suitable as a disinfectant. By using the PST, the resulting composition preferably potentiates the effect of controlling pathogenic microorganisms. By potentiating the microbicidal compositions of the present invention, lower concentrations of heavy metals can then be used to achieve a certain efficacy. Accordingly, the use of the PST and the like preferably reduces any possible detrimental and deleterious effects of these metals on the environment.

PST inhibits crystal growth and dendrites formation in metal electrodeposition; hence, the formation of smooth coherent metal surfaces is favorable. Froment, M., et al. "Influence du Tartrate Double de Sodium et de Potassium sur la Croissance des Depots Electrolytiques D'argent Obtenus a Partir d'une Solution Aqueuse de Nitrate" Comptes Rendus de L'academie des Science, Paris, t271C, pp. 253–256 (1970), incorporated in its entirety by reference herein. PST forms coherent complexes in the present invention so it can bound to silver or other metals, precluding the formation of silver crystals. The amount of the PST used in the preparation of the solution can vary, depending on the metal and the acid being used. Preferably, not more than one fourth of the equimolar portion of the PST with respect to the metal is preferably used, depending on the valency of the metal.

Thus, the PST containing microbicidal compositions of the present invention can be prepared in the same manner and are as effective, except that some or all of the amino acid groups are replaced by the PST. The PST containing microbicidal formulation can be prepared by dissolving at least one metal salt with at least one inorganic acid in an aqueous medium, and then adding the PST in its designated amount. The composition provided here may be prepared from various complexes that may form together a more complicated complex and/or complexes. The aqueous solution obtained may be concentrated and dried, and the concentrate can be made as a gel or as a solid in different forms using conventional methods available to those skilled in the art. The amount of PST used in the preparation of the solution can vary, depending on the metal and the optional amino acid being used. Preferably, not more than one fourth the equimolar portion of PST with respect to the metal should be used, depending on the valency of the metal. Preferably, slightly in excess of one fourth of the amount for univalent metal ions (e.g., Ag); at least twice as much (half) for bivalent metals (e.g. Cu), and so on. Any source of ionic M in the form of salts can be used in the present invention. For the case of silver, colloidal silver can be used as well.

Thus, the complex of the present invention can be prepared by forming the metal ion from at least one metal salt compound and PST. In the preferred process of making the organic complex of the present invention, a metal salt compound is mixed with PST alone or with at least one amino acid at room temperature (e.g., 20–30° C.) and preferably in the presence of an aqueous solution like a distilled-deionized water. Then, the organic containing compound such as PST alone or with amino acid forms the metal complex preferably while homogenizing the mixture. This preparation preferably occurs under low pH conditions, such as pH of about 2.0 or less and more preferably at a pH of 1.5 or less. The resulting solution can then be further diluted with aqueous solution and preferably distilled-deionized water and further disinfectants or other additives can be added to form the microbicidal compositions of the present invention. The aqueous solution may be condensed and dried using conventional methods available to those skilled in the art to produce gels as well as solids, such as tablets or powders.

According to the present invention, controlling the growth of at least one microorganism includes both the reduction and/or prevention of such growth. It is to be further understood that by "controlling," the growth of at least one microorganism is inhibited. In other words, there is no growth or substantially no growth of at least one microorganism. "Controlling" the growth of at least one microorganism includes maintaining a microorganism population at a desired level (including undetectable levels such as zero population), reducing a microorganism population to a desired level, and/or inhibiting or slowing the growth of at least one microorganism. Thus, materials and mediums susceptible to attack by at least one microorganism are preserved and/or protected from this attack and the resultant deleterious effects. The present invention also provides a method for controlling the growth of at least one microorganism in or on a material or medium susceptible to attack by the microorganism which comprises the step of adding to the material or medium a composition of the present invention in an amount effective to control the growth of the microorganism.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring or by metering with a suitable device so that a solution or dispersion of the composition can be produced. Thus, the substrates or materials susceptible to attack by these types of microorganisms are preserved from this attack and the resulting spoilage or other detrimental effects caused by the microorganisms. Further, it is to be understood that "controlling" the growth of at least one microorganism also includes biostatically reducing and/or maintaining a low level of microorganisms such that the attack by microorganisms and any resulting spoilage or other detrimental effects are mitigated, i.e., the microorganism growth rate or microorganism attack rate is slowed down or eliminated.

Microorganisms, as used herein, include, but are not limited to bacteria, both gram-positive and -negative, fungi, algae, viruses, amoebae, spores, and the like, and include both yeast and molds.

The biocides or microbicidal compositions of the present invention described herein have a plethora of applications and uses. They are suitable for the sterilization of drinking water, suitable for the beverage and food industry, suitable for sterilizing exposed surfaces, exhaust air and ventilation components, animal feed, suitable for use in the pharmaceutical industry, in hospitals, for surgical equipment, in swimming pools, in saunas, and for fish, poultry, and cattle farming, and the like.

The present invention is also effective in controlling biofouling. The microbicidal formulations of the present invention can be introduced directly into the source of where the biofouling is occurring or can be mixed with aqueous solutions and introduced into the area where biofouling is occurring.

Another beneficial use of the present invention is with respect to preserving or extending the life of flowers and plants. The present invention can be used as a preservative for cut flowers and cut plants by including the formulation of the present invention in the water in which the cut flowers or plants are placed into or can be formulated into a powder or tablet which can be introduced into the container holding the cut flowers or plants. Also, the formulations of the present invention can be used as a spray which is applied to living plants and flowers and acts as an agent to control pests, insects, and/or microorganisms and thus preserves a living plant and protects the plant from plant diseases, bacteria, viruses, fungus, algae, insects, and the like. The amount of the formulation which is used depends upon the plant or flowers and as described above, is typically a diluted aqueous formulation containing the microbicidal compositions of the present invention.

The present invention is further illustrated by the following non-limiting examples. These experiments constitute some of the embodiments of the invention herein disclosed. After the preparation of these disinfectants, their efficacy was then tested and evaluated against a highly resistant strain of *Pseudomonas Aeruginosa*.

EXAMPLES

Example 1

Preparation of PST-glutamic acid

At room temperature, and under minimum light, an aliquant of silver ion solution of $1.1 \times 10^5$ ppm was prepared by dissolving 400 mg of silver nitrate in 2.045 ml of doubled distilled-deionized water and 0.255 ml of 85% $H_3PO_4$. By using amicro-pipettor, 230 $\mu$l of this prepared solution was placed in a micro-tube where a specific amount of various chemical species identified in Table 1 was added and mixed thoroughly. Following mixing, the prepared solutions were then mixed with 50 ml of doubled-distilled-de-ionized water where it was stirred continuously until homogenization was achieved. Then, these samples were poured into 125 ml dark bottles where they were submitted for biological assays.

Table 1 shows the weights of glutamic acid (GA), and potassium sodium tartrate (PST) expressed in mg used. In addition, the ratio of number of moles of each chemical used (R group) with respect to the number of moles of silver used, denoted by "Ratio", is also given in Table 1. Thus, if "Ratio"=1, this represents an equimolar ratio of the corresponding chemical with respect to the initial silver concentration present in solution.

TABLE 1

| Weights of Chemicals Used (mg) | | |
|---|---|---|
| GA (mg) | PST (mg) | Ratio |
| 8.6 | 16.5 | 0.25 |
| 34.4 | 66.0 | 1.00 |
| 103.2 | 198.0 | 3.0 |

The efficacy of these samples was tested against a highly resistant strain of *Pseudomonas Aeruginosa* to determine minimum inhibitory concentration or MIC by employing serial dilutions. The minimum inhibitory concentration or MIC is defined as the minimum concentration of biocide that will inhibit the growth of the isolated microorganism. In its normal mode of operation, a bacterial inoculum is inoculated into tubes containing culture broth and varying concentrations of the antibiotic to be tested. The tubes are incubated to allow bacterial growth. The MIC is read as the lowest concentration of biocide that inhibited bacterial growth. The interpretation of this MIC depends on the organism/biocide pair being tested, and is made following standard guidelines. The biological experiments were conducted by serial dilution with Tryptic Soy Broth with Yeast Extract (TSBYE) often tubes where the bacterial concentration was 10 million cells/ml in each. The concentrate of silver complex in the first tube was 25 ppm, in the second was ⅓ of the first and so forth. Thus, the tenth tube silver complex concentration was 3.88 ppb. These tubes were then incubated at 35° C. for approximately 18 hours without agitation. The tubes were then vortexed and observed for presence and level of visible growth. The test culture was also inoculated into TSBYE (without disinfectant) to show that it was capable of rapid growth and that the growth medium was good. The growth medium was incubated (in test-tubes and in the original bottles) to show that it and the glassware were sterile. The nine disinfectants were tested for sterility (0.1 ml added to 2 ml of TSBYE). All controls turned out as expected, validating the observations of the actual experiment.

Prior to discussing the results on efficacy, several experimental observations regarding the texture and color of the complex formed with GA, TA (tartaric acid), and PST merit special mention. For comparative purposes, TA was also studied at the same silver concentrations to that of both GA and PST in an effort to examine if it forms similar complexes with silver to those of GA and PST under the existent conditions—see Gomori, J. S. "Process for Preparing a Disinfectant," U.S. Pat. No. 4,915,955, incorporated in its entirety herein by reference. The GA complex resulted in a powdery yellowish precipitate. The TA, on the other hand, did not show any formation of precipitates, and the color of the solution did not change. Finally, the PST complex gave a thick dark yellowish precipitate. These observations clearly show that the complexes formed are different for each chemical used.

Efficacy or MIC results obtained, expressed in ppm, are shown in Table 2 for three different ratios. It is important to note here that the lesser the efficacy the greater the ppm. At the same molar concentration or ratio, these data unequivocally demonstrate the superiority of the complex prepared according to the process of the present invention and the PST ppms results are less than those for GA. In Table 2, the ratio of the number of moles of PST or GA used to the number of moles of silver used are represented by "Ratio".

TABLE 2

| Efficacy Obtained (ppm). | | |
|---|---|---|
| GA (ppm) | PST (ppm) | Ratio |
| 3.34 | 2.59 | 0.25 |
| 7.78 | 2.78 | 1.00 |
| 7.78 | 2.78 | 3.0 |

Example 2

In an effort to examine the effect of mixing of GA and PST on the efficacy, several experiments were conducted at different ratios while keeping the Ratio constant. Below, Table 3 represents the amount of GA with respect to PST in (mg/mg) used for this stage at different Ratios. Notice that this was also conducted at constant Ratios. It is noteworthy to mention here that these weights actually represent the number of moles of each individual species involved with respect to silver in solution.

TABLE 3

| Relative Weights of GA:PST Used at Different Values of Ratio (mg/mg). | | | | | | | |
|---|---|---|---|---|---|---|---|
| | | 0.25 | | 1.0 | | 3.0 | |
| GA:PST(mg/mg) | Ratio = | GA | PST | GA | PST | GA | PST |
| 1:1 | | 4.30 | 8.25 | 17.2 | 33.0 | 51.6 | 99.0 |
| 1:2 | | 2.87 | 11.0 | 11.5 | 44.1 | 34.4 | 132.0 |
| 2:1 | | 5.73 | 5.50 | 22.9 | 22.0 | 68.8 | 66.0 |

The results obtained on efficacy are depicted in Table 4. The efficacy was determined in the same manner to that of Example 1. By comparing Tables 2 and 4, one can see that the addition of GA to PST decreases the efficacy. Notice here that when GA:PST is 1:2, and Ratio=1, similar results to that for pure PST at Ratio=1 are observed (see Table 2). In addition, efficacy results are strong function of Ratio. In general, these experimental observations unequivocally demonstrate that mixing GA and PST is not favorable; however, PST can be used as a potentiator for GA under certain circumstances.

TABLE 4

| Efficacy Obtained on the GA:PST at Different Values of Ratio. | | | | |
|---|---|---|---|---|
| GA:PST(mg/mg) | Ratio = | 0.25 | 1.0 | 3.0 |
| 1:1 | | 3.34 | 8.33 | 7.78 |
| 1:2 | | 8.33 | 2.78 | 7.78 |
| 2:1 | | 8.33 | 7.78 | 3.34 |

Although the present invention has been described with reference to certain preferred embodiments, other variations are possible. Therefore, the spirit and scope of the appended claims should not be limited to the description contained herein.

The previous explanation and the illustrations and procedures set forth above are solely intended for the purpose of setting out the generic and general embodiments of the present invention. Therefore, it is to be understood that the present invention by no means is limited to the specific features disclosed herein, and such details can be varied by those skilled in the art in consideration of the present specification and practiced without departing from the true scope and merits of the invention.

What is claimed is:

1. A microbicidal composition comprising an organometallic chelate containing at least one microbicidal metal cation and potassium sodium tartrate or an ion of potassium sodium tartrate, wherein the potassium sodium tartrate is present in at least one fourth of the molar amount of the microbicidal metal cation multiplied by the valency number of the microbicidal metal cation, and wherein said composition is prepared under acidic conditions using at least one inorganic acid.

2. The microbicidal composition of claim 1, wherein the microbicidal metal cation comprises a silver ion or colloidal silver.

3. The microbicidal composition of claim 1, wherein the microbicidal metal cation is a cation of copper, zinc, mercury, chromium, manganese, nickel, cadmium, arsenic, cobalt, aluminum, iron, lead, selenium, platinum, gold, titanium, tin, barium, vanadium, bismuth, strontium, antimony, or combinations thereof.

4. The microbicidal composition of claim 1, further comprising an aqueous solution.

5. A method for preparing the microbicidal chelate composition of claim 1, comprising preparing an aqueous solution of a microbicidal metal cation (M) in dilute acid to form an acid solution, wherein said acid solution contains at least one inorganic acid;

adding potassium sodium tartrate in an amount that is at least one fourth of the molar amount of the microbicidal metal cation multiplied by the valency number of the microbicidal metal cation to the acid solution; and mixing the solution with water and stirring until a homogenized solution is achieved.

6. The method of claim 5, wherein the aqueous solution of said microbicidal metal cation has a pH of 2.0 or less.

7. The method of claim 5, wherein M comprises silver.

8. The method of claim 5, further comprising the step of separating the microbicidal composition as a solid from a homogenate.

9. The microbicidal composition of claim 1 further comprising a complex of the formula R-M, wherein R is at least one organic chelating moiety and M is at least one metal ion, and where R is present in an at least equimolar amount based on the amount of M, and M is microbicidal to at least one microorganism.

10. The microbicidal composition of claim 1, wherein said composition is in the form of a gel or solid.

11. The microbicidal composition of claim 9, wherein said at least one metal ion is a silver ion or colloidal silver.

12. The microbicidal composition of claim 9, wherein said at least one metal ion is an ion of copper, zinc, mercury, chromium, manganese, nickel, cadmium, arsenic, iron, cobalt, aluminum, lead, selenium, platinum, gold, titanium, tin, barium, vanadium, bismuth, stontium, antimony, or combinations thereof.

13. The microbicidal composition of claim 9, wherein said at least one organic chelating moiety comprises at least one amino acid.

14. The microbicidal composition of claim 1, further comprising at least one other disinfectant or natural or artificial flavors or colorants or both.

15. The microbicidal composition of claim 9, wherein said at least one organic chelating moiety is formed from an alpha-amino acid.

16. The microbicidal composition of claim 9, wherein said at least one organic chelating moiety is selected from isoleucine, phenylalanine, leucine, lysine, methionine, threonine, tryptophan, valine, alanine, glycine, arginine, histidine, and mixtures thereof.

17. A method to control the growth of microorganisms comprising contacting the microorganisms with an effective amount of a microbicidal composition comprising the microbicidal composition of claim 1.

18. A method to control biofouling in a system, comprising introducing an effective amount of said microbicidal composition of claim 1 to said system to control said biofouling.

19. The microbicidal composition of claim 1, wherein the molar ratio of potassium sodium tartrate or an ion of potassium sodium tartrate to the microbicidal metal cation is from about 0.25:1 to about 3:1.

20. The microbicidal composition of claim 1, wherein said microbicidal composition is present in an aqueous solution at a concentration of from about 0.001% to about 10% by total volume.

21. The microbicidal composition of claim 1, further comprising at least one other disinfectant.

22. The microbicidal composition of claim 21, wherein said at least one disinfectant comprises one or more of isopropyl alcohol, hydrogen peroxide, chlorhexidine gluconate, chlorhexidine digluconate, chlorhexidine dihydrochloride, or chlorhexidine diacetate.

23. The microbicidal composition of claim 1 further comprising a product obtained by combining at least one metal ion (M) with at least an equimolar amount of at least one organic chelating moiety (R) based on the amount of M, wherein M is microbicidal to at least one microorganism.

24. The microbicidal composition of claim 23, wherein said at least one organic chelating moiety comprises an amino acid.

25. The microbicidal composition of claim 23, wherein said at least one metal ion is a silver ion or colloidal silver.

26. A method to control the growth of a microorganism susceptible to treatment with a metal ion, said method comprising:

treating said microorganism with an effective amount of the microbicidal composition of claim 23.

27. A method of controlling biofouling in a system, comprising introducing to said system an effective amount of the microbicidal composition of claim 23.

28. The microbicidal composition of claim 1 further comprising a complex of the formula R-M, wherein R is at least one organic chelating moiety and M is at least one metal ion, and where R is present in an at least equimolar amount based on the amount of M, and M is microbicidal to at least one microorganism, wherein said at least one organic chelating moiety is formed from an amino acid, and said organic chelating moiety has a carboxylic group which forms a dative covalent bond with M.

29. The microbicidal composition of claim 1, further comprising at least one amino acid.

30. The method of claim 5, wherein said acid solution is prepared under room temperature.

* * * * *